(12) United States Patent
Gradtke et al.

(10) Patent No.: US 8,765,795 B2
(45) Date of Patent: Jul. 1, 2014

(54) ISOTHIAZOLONE-CONTAINING PRESERVATIVE WITH IMPROVED EFFECTIVENESS

(75) Inventors: Ralf Gradtke, Tornesch (DE); Wolfgang Beilfuss, Hamburg (DE); Petra Kolditz, Hamburg (DE)

(73) Assignee: Air Liquide Sante (International), Paris (FR)

( * ) Notice: Subject to any disclaimer, the term of this patent is extended or adjusted under 35 U.S.C. 154(b) by 435 days.

(21) Appl. No.: 13/290,199

(22) Filed: Nov. 7, 2011

(65) Prior Publication Data

US 2012/0053215 A1    Mar. 1, 2012

Related U.S. Application Data

(62) Division of application No. 11/885,451, filed as application No. PCT/EP2006/060383 on Mar. 2, 2006, now Pat. No. 8,076,363.

(30) Foreign Application Priority Data

Mar. 16, 2005    (DE) .......................... 10 2005 012 123

(51) Int. Cl.
*A01N 43/80*    (2006.01)
*A61K 31/425*    (2006.01)

(52) U.S. Cl.
USPC .......................................................... 514/372

(58) Field of Classification Search
None
See application file for complete search history.

(56) References Cited

U.S. PATENT DOCUMENTS

| | | |
|---|---|---|
| 4,940,615 A | 7/1990 | Hammer |
| 5,127,934 A | 7/1992 | Mattox |
| 5,147,884 A | 9/1992 | Diehl |
| 5,516,510 A | 5/1996 | Beilfuss |
| 5,591,442 A | 1/1997 | Diehl |
| 5,618,832 A | 4/1997 | Schmidt |
| 5,646,105 A | 7/1997 | Hachmann |
| 2005/0154067 A1 | 7/2005 | Beilfuss |

FOREIGN PATENT DOCUMENTS

| | | |
|---|---|---|
| EP | 0 330 996 | 9/1989 |
| EP | 0 450 916 | 10/1991 |
| EP | 0 530 986 | 3/1993 |
| EP | 0 599 433 | 6/1994 |
| EP | 1 537 781 | 6/2005 |

*Primary Examiner* — Anna Pagonakis
(74) *Attorney, Agent, or Firm* — Young & Thompson

(57) ABSTRACT

A preservative which comprises a) one or more isothiazolones and b) one or more glycerol monoalkyl ethers, and the use of the preservative for microbicidal finishing of cosmetic and pharmaceutical products.

2 Claims, No Drawings

ISOTHIAZOLONE-CONTAINING PRESERVATIVE WITH IMPROVED EFFECTIVENESS

The present invention relates to a preservative which comprises a) one or more isothiazolones and b) one or more glycerol monoalkyl ethers, to the use of the preservatives for the microbicidal finishing of cosmetic and pharmaceutical products, and to corresponding microbicidally finished products, in particular cosmetic and pharmaceutical preparations, technical products, household products, cooling lubricant concentrates and emulsions, and pack preservatives.

Preservatives are used in many aqueous systems in order to control microbial growth. An important field of use is cosmetic formulations, such as creams, lotions, sunscreen products, shampoos, shower gels and bath additives. Preservatives are also used in cleaning, care and hygiene products for the home (e.g. hand washing preparations), and in many technical sectors.

However, there continues to be a great need for improved compositions which have a broad spectrum of activity towards bacteria, yeasts, moulds and viruses, develop their biocidal effectiveness (killing of microorganisms) under conditions met in practice even at low use concentrations and—something which is particularly important for cosmetic and pharmaceutical preparations—have good physiological compatibility.

It is known that glycerol monoalkyl ethers have antimicrobial effects. For Example, DE 42 40 674 A1 relates to deodorizing glycerol monoalkyl ethers, the alkyl group specified being the 2-ethylhexyl group. The monoalkyl glycerol ethers can be used in combination with one or more other deodorizing substances. Of particular suitability is 1-(2-ethylhexyl) glycerol ether, which is available under the trade name Sensiva SC 50® (Schülke & Mayr GmbH, Germany). However, glycerol monoalkyl ethers on their own do not have a broad spectrum of activity towards Gram-positive and Gram-negative bacteria, fungi, yeasts and viruses.

Also known, for example from EP 530 986 A2, are isothiazolin-3-ones (isothiazolones) as effective bactericidal and fungicidal active ingredients in cooling lubricants for metalworking.

The present invention was based on the object of providing preservatives specifically for cosmetic and pharmaceutical products which have a broad spectrum of activity even at a low use concentration. The preservatives should themselves be storable over a long period.

Surprisingly, it has now been found that this object is achieved by a combination of
a) one or more isothiazolones with
b) one or more 1- or 2-($C_1$- to $C_{24}$-alkyl)glycerol ethers (glycerol monoalkyl ethers).

The invention is based inter alia on the fact that it has been found that for a certain microbicidal finishing in each case a smaller amount of components a) and b) is necessary or for a certain amount of components a) and b) a higher level of microbicidal finishing is achieved.

Moreover, it has been found that the combination is microbicidally effective even in the absence of a mixture of two or more different aromatic alcohols (b1, b2) chosen from the groups of i) aryloxyalkanols, ii) arylalkanols and iii) oligoalkanol aryl ethers if the two different aromatic alcohols belong to different groups i), ii) and iii). In all embodiments of the invention, the presence of i) aryloxyalkanols, ii) arylalkanols and iii) oligoalkanol aryl ethers is preferably excluded, the presence of aromatic alcohols more preferably being excluded.

It was also surprising that the effectiveness of glycerol monoalkyl ethers, which have hitherto been used primarily on account of their deodorizing effect, and the effectiveness of isothiazolones, which have hitherto been used as preservatives for cooling lubricants for metalworking, complement one another in such a way that the combination has broad microbicidal effectiveness even at a low concentration. This low concentration has good physiological compatibility. For a corresponding effectiveness of the individual components, not only would significantly larger amounts of the components have to be used, which would be associated with corresponding costs, but the use of such larger amounts would also be associated with disadvantages (such as with difficulties during formulation and physiological incompatibility of relatively large amounts). These disadvantages do not arise with the combination according to the invention. For example, the maximum permitted concentration of methylisothiazolone in cosmetic preparations is 100 ppm, which in many cases leads to inadequately preserved highest end products. As a result of combination with glycerol ethers, products which are preserved with at most 100 ppm of methylisothiazolone are reliably protected against microbial decomposition.

Isothiazolone

Suitable isothiazolones are known to the person skilled in the art for example from the above-mentioned EP 530 986 A2. Isothiazolones used according to the invention are preferably chosen from 2-methyl-isothiazolone (methylisothiazolone), 5-chloro-2-methylisothiazolone, 2-n-octylisothiazolone, benzo-isothiazolone, 4,5-dichloro-2-n-methylisothiazolone, 4,5-dichlorooctylisothiazolone and n-butylbenzo-isothiazolone, preference being given to methylisothiazolone, 4-chloro-2-methylisothiazolone, 2-n-octylisothiazolone, benzoisothiazolone and mixtures thereof. Particular preference is given to methylisothiazolone.

Glycerol Monoalkyl Ethers

Suitable glycerol monoalkyl ethers are known to the person skilled in the art, e.g. from DE 42 40 674 A1. The alkyl group of the glycerol monoalkyl ether is preferably a branched or unbranched $C_3$- to $C_{18}$-alkyl group, where the alkyl group may be substituted by one or more hydroxyl and/or $C_1$- to $C_4$-alkoxy group(s) and/or the alkyl chain may be interrupted by up to 4 oxygen atoms. 1-Monoalkyl glycerol ethers are preferred.

Use is made, for example, of glycerol monoalkyl ethers with an alkyl group which is a branched or unbranched $C_3$- to $C_{18}$-hydrocarbon group, preferably a branched or unbranched $C_6$- to $C_{12}$-hydrocarbon group, preferably a branched or unbranched octyl group and in particular a 2-ethylhexyl group.

Examples of glycerol monoalkyl ethers used according to the invention are glycerol monoalkyl ethers substituted in the 1 or 2 position (i.e. symmetrical or asymmetrical) by saturated or unsaturated, branched or unbranched alkyl, such as dodecyl glycerol ether, decyl glycerol ether, nonyl glycerol ether, octyl glycerol ether, hexyl glycerol ether, propyl glycerol ether, octadecyl glycerol ether (batyl alcohol), hexadecyl glycerol ether (chimyl alcohol), menthyl glycerol ether and octadecenyl glycerol ether (selachyl alcohol). Preference is given to using 1-monoalkyl glycerol ethers. Very particular preference is given to 1-(2-ethylhexyl)glycerol ether and dodecyl glycerol ether. In a preferred general embodiment of the invention a) the isothiazolone is methylisothiazolone and b) the glycerol monoalkyl ether is 1-(2-ethylhexyl)glycerol ether.

In one embodiment, the invention relates to a preservative which comprises the combination and is in the form of a concentrate, where the presence of a mixture of two or more different aromatic alcohols (b1, b2) chosen from the groups of i) aryloxyalkanols, ii) arylalkanols and iii) oligoalkanol aryl ethers is excluded if the two different aromatic alcohols belong to different groups i), ii) and iii). Besides the components (a) and (b) according to the invention, the preservative according to the invention can comprise further components. The further components may be solid, liquid or gaseous further active ingredients, functional additives or auxiliaries. Examples of further active ingredients, functional additives and auxiliaries are: complexing agents, such as EDTA, NTA, phosphonates, glycine derivatives, octaquest (trisodium ethylenediaminedisuccinate), quats, such as benzalkonium chloride, benzethionium chloride, organo-halogen compounds, such as IPBC, DBDCB, Bronopol, and others, solvents and solubility promoters, such as water, alcohols, glycols, glycol ethers, polyols (e.g. 1,2-pentanediol, 1,2-hexanediol, 1,2-octanediol, glycerol, 1,2-propylene glycol, butylene glycol and others), metal salts, such as Cu salts, Ag salts, Zn salts and others. Preference is given to using organohalogen-free further additives. The combination of the preparations according to the invention with the further components can lead to synergistic increases in effectiveness.

Preference is given here to concentrates which consist essentially of the two components a) and b), it being possible, if required, to add a small amount (for example to 20% by weight, preferably 0.5 to 10% by weight, in particular 1 to 3% by weight, such as, for example, 2% by weight) of solvents and/or solubility promoters.

In the concentrate according to the invention, the preferred amount of component a) is 0.1 to 30% by weight, preferably 1 to 20% by weight, more preferably 3 to 5% by weight, in particular 5 to 10% by weight, such as about 8% by weight. In addition, in the concentrate according to the invention the preferred amount of component b) is 99.9 to 70% by weight, preferably 99 to 80% by weight, more preferably 96 to 85% by weight, in particular 93 to 88% by weight, such as, for example, 90% by weight.

In a very preferred embodiment, the preservative comprises about 8% by weight of 2-methylisothiazolone and about 90% by weight of 1-(2-ethylhexyl)glycerol ether in about 2% by weight of solvent or diluent (e.g. water).

In a further embodiment, the preservative concentrate comprises 0.1 to 30% by weight of component a), 0.1% to 30% by weight of component b) and optionally further components such as solvents, e.g. water, alcohols, glycols, glycol ethers or polyols.

Moreover, the invention relates to the use of the preservative according to the invention or of a combination of components a) and b) for the microbicidal finishing of products. According to the invention, the use is characterized in that for a certain microbicidal finishing a smaller amount of the particular component is necessary or for a certain amount of the particular component a higher level of microbicidal finishing is achieved. Alternatively, the use according to the invention is characterized in that in the microbicidally finished product the presence of a mixture of two or more different aromatic alcohols (b1, b2) chosen from the groups of i) aryloxyalkanols, ii) arylalkanols and iii) oligoalkanol aryl ethers if the two different aromatic alcohols belong to different groups i), ii) and iii) is excluded.

The invention also relates to products (preferably cosmetic and pharmaceutical products) which comprise the combination according to the invention besides customary ingredients. Due to the particular physiological compatibility, combinations according to the invention have a broad field of use. The preservatives and products may be in the form of clear, homogeneous, e.g. aqueous preparations, or in the form of low-viscosity or high-viscosity preparations, e.g. gels. The combination is effective over a broad pH range and can be used in strongly acidic to strongly alkaline media, preferably in the pH range from 3 to 11, particularly preferably 5 to 9. The preservatives may also be in the form of dispersions, semisolid preparations, such as pastes, or in the form of solids (e.g. powders, granules).

Examples of preparations referred to here as product are:

1) dermatological and cosmetic products, e.g. for topical application or as leave-on or rinse-off products, such as sunscreen preparations, wet wipes, polymeric preparations with film-forming properties, toothpastes, care products, makeup, lipsticks, nail varnish, 2) pharmaceutical preparations such as isotonic solutions, medicaments and vaccines, and 3) disinfectant preparations, such as deodorants, foot deodorants, alcoholic spray disinfectants and compositions for manual instrument preparation.

4) Household products, such as cleaners, detergents, fabric softeners, dishwashing detergents and other, technical products, such as paints, dispersions, adhesives, emulsions and others.

Products microbicidally finished according to the invention are, in particular, cosmetic and pharmaceutical preparations, technical products, household products, cooling lubricant concentrates and emulsions, and pack preservatives.

Surfaces with which products stabilized according to the invention can be treated are i) biological materials, such as skin, mucosa, wounds, plants, parts of plants (animate surfaces), and ii) materials which come into contact with the skin, mucosa or wounds, such as contact lenses or wound coverings, e.g. surfaces which come into contact with the products stabilized according to the invention, such as animate and inanimate surfaces and others (hard surfaces).

The present invention offers, inter alia, the following advantages:

The combinations are formulated from cost-effective components.

The combinations are pH neutral, not very aggressive (low corrosion) and correspondingly good to sufficiently material-compatible.

The combinations and preservatives are low-odour, low-emission, inert and good to adequately compatible with other additives or auxiliaries, toxicologically and ecotoxicologically acceptable, physiologically acceptable (good to adequate skin compatibility), readily to adequately removable by rinsing.

The combinations are low-foam and oxidation- and pH-stable.

Added to this is the fact that according to the invention the desired high effectivenesses can surprisingly be achieved which are physically not possible (due to the limited solubility of these substances in water) or permissible (due to prescribed maximum amounts of (methyl)isothiazolone) with noninventive combinations of a) isothiazolone and b) glycerol monoalkyl ethers. Finally, the components also have a synergistic effect and the chosen final concentration of the combination according to the invention in the (microbicidally finished) products to be preserved can be comparatively low despite the required high effectiveness.

The combinations according to the invention thus solve the abovementioned problems in the prior art and have good stability on account of a low active ingredient fall-off during storage, insensitivity to low and high pH values, to low and high temperatures (they have low-temperature stability, thermostability), and to oxidizing agents and reducing agents and good compatibility with customary ingredients of cosmetic and pharmaceutical products, they thus represent a good alternative to other "soft" preservatives such as parabens.

The combinations according to the invention have broad effectiveness against bacteria, yeasts, fungi and viruses, and also against "problem germs", such as odour-causing microorganisms, microorganisms which "cause skin/hair problems (dandruff, acne, blemished skin)", such as *Malassezia furfur, Propionibacterium acnes* and others.

Preferred combinations according to the invention are also liquid at low temperatures and thus can be handled and metered easily. Preferably, the antioxidants disclosed in DE 100 28 638 are used. In particular, the addition of tocopherol and its derivatives (such as vitamin E) as antioxidant suppresses the destabilization of products containing glycerol monoalkyl ethers (such as 1-(2-ethylhexyl)glycerol ether).

In the microbicidally finished product, the total amount of components a) and b) in the combination according to the invention is preferably 100 to 10 000 ppm (0.01 to 1% by weight), preferably 500 to 5000 ppm, such as about 1000 ppm. Here, preferred amounts of the components are a) 8 to 800 ppm, more preferably 40 to 400 ppm or 50 to 160 ppm, such as about 80 ppm, and/or b) 90 to 9000 ppm, more preferably 450 to 4500 ppm, in particular 630 to 1800 ppm, such as about 900 ppm.

The advantages of the present invention are particularly evident from the examples below.

EXAMPLES

Materials Used

Neolone=Neolone ® 950, a 9.5% strength solution of methylisothiazolone in water;

Sensiva=Sensiva® SC 50, 1-(2-ethylhexyl)glycerol ether;

Carbopol=Carbopol® ETD 2020, crosslinked polyacrylic acid copolymer.

The following standard formulations A) and B) were used:

A) Standard Gel

| | |
|---|---|
| Glycerol, 85% | 120.0 g |
| Carbopol | 3.2 g |
| Demineralized water | 674.4 g |
| NaOH, 45% | 2.4 g |

Carbopol is dispersed in glycerol. In batches, the water and then NaOH are added thereto. The gel immediately becomes thick.

B) Humectant Formulation 6940

In accordance with Seppic formulation procedure, without preservative.

Method of Determining the Preserving Effect of Chemical Preservatives in Cosmetic Formulations Principle Using the described method, the effectiveness of chemical preservatives is tested with regard to the pack preservation for cosmetic formulations. For this purpose, in various experimental batches, the preservatives to be investigated are added to the unpreserved samples in various concentrations. A continuous germ burden is achieved by periodically inoculating the experimental batches. In parallel to the inoculation, streaks of each of the individual batches are in each case made immediately beforehand. Assessment is made by reference to the microbial growth of the streaks. The longer the period before the first appearance of microbial growth, the more effective a preservative.

Solutions and Nutrient Media

| | |
|---|---|
| CSA (casein peptone soya flour peptone agar | Oxoid CM 131 |
| SA (Sabouraud agar) | Oxoid CM 41 |
| Sterile 0.85% (w/v) NaCl solution | |

Test Germs

| Bacteria | |
|---|---|
| *Kocuria rhizophila* | ATCC 9341 |
| *Staphylococcus aureus* | ATCC 6538 |
| *Enterobacter gergoviae* | ATCC 33028 |
| *Escherichia coli* | ATCC 11229 |
| *Klebsielle pneumoniae* | ATCC 4352 |
| *Pseudomonas aeruginosa* | ATCC 15442 |
| *Pseudomonas fluorescens* | ATCC 17397 |
| *Pseudomonas putida* | ATCC 12633 |
| Yeasts | |
| *Candida albicans* | ATCC 10231 |
| Fungi | |
| *Aspergillus niger* | ATCC 6275 |
| *Penicillium funiculosum* | ATCC 36839 |

Cultivation of the Test Germs

The bacteria are streaked uniformly over the entire surface of a CS nutrient medium using a sterile glass rod and incubated for 24 h at 30±1° C. The yeast *C. albicans* is streaked using a sterile glass rod on a Sabouraud nutrient medium and incubated for 48 h at 30±1° C.

The laboratory cultures of the bacteria and of the yeast *C. albicans* are replaced every 4 weeks.

The fungi *A. niger* and *P. funiculosum* are streaked using a sterile glass rod on one (*A. niger*) or two (*P. funiculosum*) Sabouraud plates (comprising 100 µg/ml of gentamycin and 50 µg/ml of chloramphenicol) and incubated for 7 to 14 days at 25±2° C.

The laboratory cultures of the fungi *A. niger* and *P. funiculosum* are transferred every 3 weeks.

The strain cultures are replaced every 12 months.

Preparation of the Starting Fungi Suspensions

To prepare the mixed suspension, starting suspensions of *A. niger* and *P. funiculosum* are firstly prepared:

*Aspergillus niger:*

A 7 to 14 day old Sabouraud plate is rinsed off with 10 ml (2×5 ml) of sterile 0.85% NaCl solution (w/v). The fungus suspension rinsed off is poured through a filter with glass wool (sterile) into a sterile 100 ml measuring cylinder and made up to 100 ml with sterile 0.85% NaCl solution. The *A. niger* suspension obtained in this way is then transferred to a sterile glass-stoppered bottle containing sterile glass beads.

Titre of the *A. niger* suspension: ~$10^7$ CFU/ml.

*Penicillium funiculosom:*

Two 7 to 14 day old Sabouraud plates are rinsed off with 10 ml (2×5 ml) of sterile 0.85% NaCl solution (w/v). The rinsed-off fungi suspensions are poured through a filter containing glass wool (sterile) into a sterile 100 ml measuring cylinder and made up to 100 ml with sterile 0.85% NaCl solution. The *P. funiculosum* suspension obtained in this way is then transferred to a sterile glass-stoppered bottle containing sterile glass beads.

Titre of the *P. funiculosum* suspension: ~$10^{6-7}$ CFU/ml.

The fungi suspensions prepared as described above are stored for 3 weeks in a refrigerator at 5° C.±2° C. and can be used within this time. Prior to use for the preparation of the mixed suspension, the fungi suspensions have to be shaken briefly in order to obtain a homogeneous suspension.

The titre of the starting fungi suspensions is monitored at least quarterly.

Preparation of the Mixed Suspensions

To prepare the mixed suspensions, the bacteria, per strain one plate, are rinsed off with 5 ml of a sterile 0.85% NaCl solution per CSA plate, (sterile) filtered through a sterile glass funnel containing glass wool and made up to 150 ml with 0.85% NaCl solution. This bacteria suspension has a titre of $\sim 10^{10}$ CFU/ml.

The yeast *C. albicans* is likewise rinsed off with 10 ml of sterile 0.85% NaCl solution from a Sabouraud plate and (sterile) filtered through a sterile glass funnel containing glass wool. 10 ml of each of the fungi suspensions (*A. niger* and *P. funiculosum*) prepared as described above are added to this suspension. 3 ml of the bacteria suspension prepared as described above (titre $\sim 10^{10}$ CFU/ml) are added. The resulting mixed suspension is made to 150 ml with sterile 0.85% NaCl solution.

The bacteria titre of the mixed suspension is $\sim 10^8$ CFU/ml. The titre for *C. albicans* in the mixed suspension is $\sim 10^8$ CFU/ml. The titre for *A. niger* and *P. funiculosum* in the mixed suspension is $\sim 10^6$ CFU/ml.

The titre in the mixed suspension is monitored at least quarterly.

Implementation

In separate batches, 25 or 50 g of the material to be preserved are in each case admixed with varying concentrations of the preservative to be investigated. The growth control used in each case is an unpreserved product sample.

The test batches are streaked onto CS and Sabouraud nutrient media once per week, the first streaking being carried out directly prior to reinoculation; these batches are then inoculated with the mixed suspension (in the case of 25 g samples with 0.1 ml, in the case of 50 g samples with 0.2 ml). The inoculated samples are incubated at 25° C.±2° C. over the entire experimentation period.

The microbial growth of the streaks incubated at 25° C.±2° C. is assessed after 3 to 4 days. To be on the safe side, negative streaks are observed for a further 2 days and reassessed. The preserving effect of the individual product concentrations is assessed in a semiquantitative method by means of the growth of the individual streaks according to the grading from "–" via "+" to "+++". The test is usually carried out over 6 inoculation cycles or terminated after massive growth (+++) on two occasions.

If even after five successive inoculation cycles growth can be detected neither in the preserved samples nor in the unpreserved product sample (blank value), then the inoculation in the sixth inoculation cycle is carried out with five times the amount of the mixed suspension (0.5 ml in the case of 25 g samples, 1 ml in the case of 50 g samples).

Assessment of the Results

A preservative is considered good if it exists under the laboratory conditions given above for a period of 6 weeks without germ infestation of the sample batches, i.e. even after the sixth inoculation, no microbial growth can be detected.

Legend:
−=no growth
−=slight growth
++=moderate growth
+++=massive growth
Y=yeasts
F=fungi
B=bacteria Example 1

Antimicrobial effectiveness in formulation 6940

| Preservative | 4 days | 10 days | 17 days | 25 days |
|---|---|---|---|---|
| without | − | +++ (B, Y, F) | +++ (B, Y, F) | |
| Neolone | | | | |
| 0.05% | − | ++ (B, Y) | +++ (B, Y) | +++ (Y) |
| 0.1% | − | + (Y) | + (Y) | |
| Sensiva | | | | |
| 0.1% | − | +++ (B, Y, F) | +++ (B, Y, F) | |
| 0.2% | − | +++ (B, Y, F) | +++ (B, Y, F) | |
| 0.3% | − | +++ (B, Y, F) | +++ (B, Y, F) | |
| Neolone (0.1%) + Sensiva (0.1%) | − | − | − | − |

Example 2

| Preservative | 3 days | 10 days | 17 days | 24 days | 31 days | 38 days | 45 days |
|---|---|---|---|---|---|---|---|
| Antimicrobial effectiveness in the standard gel | | | | | | | |
| without | − | ++ (F) +++ (B) | ++ (F) +++ (B) | | | | |
| Neolone, 0.1% | | +++ (F) | +++ (B, F) | | | | |
| Sensiva, 0.1% | | +++ (F) | +++ (B, F) | | | | |
| Neolone, 0.1% + Sensiva, 0.1% | − | − | − | − | − | − | − |
| Neolone, 0.05% + Sensiva, 0.1% | − | − | − | − | − | − | + (B) |

Result: The abovementioned results for Examples 1 and 2 demonstrate that isothiazolones and glycerol ethers surprisingly complement one another in their effectiveness.

The invention claimed is:

1. A method for microbicidal finishing of a product, comprising:
   applying to said product a composition comprising
   a) from 50 to 160 ppm of 2-methylisothiazolone; and
   b) from 630 to 1800 ppm of 1-(2-ethylhexyl) glycerol ether,
   wherein in said product a mixture of two or more different aromatic alcohols selected from the group consisting of i) aryloxyalkanols, ii) arylalkanols and iii) oligoalkanol aryl ethers is excluded if two different aromatic alcohols belong to different groups i), ii) and iii)).

2. The method according to claim 1, wherein the product is a cosmetic or pharmaceutical formulation and comprises a) about 0.008% by weight of 2-methylisothiazolone and b) 0.09% by weight of 1-(2-ethylhexyl) glycerol ether.

* * * * *